United States Patent
Pasini et al.

(10) Patent No.: US 7,751,526 B2
(45) Date of Patent: Jul. 6, 2010

(54) METHOD FOR SYNCHRONISING AN EMITTER AND A DETECTOR IN A COMPUTED TOMOGRAPHY SCANNER

(75) Inventors: Alessandro Pasini, Cesena (IT); Dario Righini, Imola (IT); Eros Nanni, Castel Guelfo Di Bologna (IT)

(73) Assignee: Cefla Societa'Cooperativa, Imola (IT)

( * ) Notice: Subject to any disclaimer, the term of this patent is extended or adjusted under 35 U.S.C. 154(b) by 148 days.

(21) Appl. No.: 12/051,621

(22) Filed: Mar. 19, 2008

(65) Prior Publication Data

US 2008/0232544 A1    Sep. 25, 2008

(30) Foreign Application Priority Data

Mar. 20, 2007   (EP)   ................................... 07425159

(51) Int. Cl.
   *G01N 23/083*   (2006.01)
   *H05G 1/56*   (2006.01)
   *H05G 1/58*   (2006.01)
   *H05G 1/64*   (2006.01)

(52) U.S. Cl. .......................... 378/19; 378/62; 378/98.8; 378/101; 378/114

(58) Field of Classification Search ..................... 378/4, 378/19, 62, 96, 98.8, 101, 108, 114–116; 250/370.09, 370.11, 371

See application file for complete search history.

(56) References Cited

U.S. PATENT DOCUMENTS

| 4,532,644 | A | | 7/1985 | Yamaguchi et al. |
| 5,379,334 | A | * | 1/1995 | Zimmer et al. ............. 378/98.2 |
| 5,940,470 | A | * | 8/1999 | Palm-Plessmann et al. . 378/197 |
| 6,104,780 | A | * | 8/2000 | Hanover et al. ............... 378/92 |
| 6,381,299 | B1 | | 4/2002 | Baba et al. |
| 7,154,994 | B2 | * | 12/2006 | Gray .......................... 378/116 |
| 2006/0008048 | A1 | | 1/2006 | Katada et al. |

FOREIGN PATENT DOCUMENTS

| EP | 0358828 | 3/1990 |
| EP | 1161122 | 12/2001 |
| WO | 03/032839 | 4/2003 |

* cited by examiner

*Primary Examiner*—Edward J Glick
*Assistant Examiner*—Thomas R Artman
(74) *Attorney, Agent, or Firm*—Fish & Richardson P.C.

(57) ABSTRACT

In a computed tomography scanner provided with an emitter for emitting a beam of radiation through an object to be analyzed and a detector for acquiring radiographies of the object, the detector generates a synchronization signal corresponding to its state of activation for acquiring the radiographies, and the emitter is controlled via the synchronization signal in such a way that the beam of radiation will be emitted when the detector is already activated.

15 Claims, 2 Drawing Sheets

METHOD FOR SYNCHRONISING AN EMITTER AND A DETECTOR IN A COMPUTED TOMOGRAPHY SCANNER The present invention relates to a method for synchronising an emitter and a detector in a computed tomography scanner.

In particular, the present invention finds advantageous, but not exclusive, application in computed tomography scanners used in the sector of dentistry, to which the ensuing description will make explicit reference, without this implying any loss of generality.

BACKGROUND OF THE INVENTION

In the sector of dentistry computed tomography scanners are used, in the present state of the art, of the type comprising an x-ray source-detector assembly designed to rotate about an area of analysis in which the head of a patient is positioned for acquiring volumetric tomographic data of one or both of the dental arches of the patient. The source-detector assembly comprises a rotating support, typically constituted by an arm that is motor-driven so as to rotate about a horizontal axis traversing said area of analysis, an x-ray emitter, mounted on a first end of the arm for emitting an x-ray beam through the area of analysis, and an x-ray detector, mounted on the opposite end of the arm and facing the emitter for receiving the beam after it has traversed the area of analysis.

The tomography scanner 1 further comprises a control unit, connected to the source-detector assembly for controlling emission and reception of the beam in a way synchronous with rotation of the arm, and a processing unit connected to the detector for receiving, storing, and processing the volumetric tomographic data so as to reconstruct images of the object.

In particular, the control unit generates a first signal for operating the detector for a given exposure time, and a second signal for operating the emitter so that it emits an x-ray beam only after the detector has been operated to prevent useless doses of x-rays from being administered to the patient. The two signals for operation, respectively, of the detector and of the emitter are generated starting from a single pre-defined synchronisation signal, generated by the control unit, for example as a function of the angular position of the arm.

The fact of having a number of units, i.e., the emitter and the detector, controlled according to a single synchronisation signal generated by a control unit, gives rise to latency times due to the propagation of the synchronisation signal along the connections between the control unit and the various controlled units, said latency times not always being predictable and being of the order of magnitude of the times involved, i.e., of the order of magnitude of a few microseconds or of some tens of microseconds. Said latency times generate synchronisation errors between the controlled units.

SUMMARY OF THE INVENTION

The aim of the present invention is to provide a method for synchronizing an emitter and a detector in a computed tomography scanner and to provide a detector for a computed tomography scanner and a computed tomography scanner implementing said method that will enable the drawback described above to be overcome and, at the same time, will be easy and inexpensive to implement.

According to the present invention a method for synchronising an emitter and a detector in a computed tomography scanner, a detector for a computed tomography scanner and a computed tomography scanner are provided as claimed in the attached claims.

BRIEF DESCRIPTION OF THE DRAWINGS

For a better understanding of the present invention, a preferred embodiment is now described, purely by way of non-limiting example and with reference to the attached plates of drawings, wherein.

DETAILED DESCRIPTION OF THE INVENTION

Figure 1:
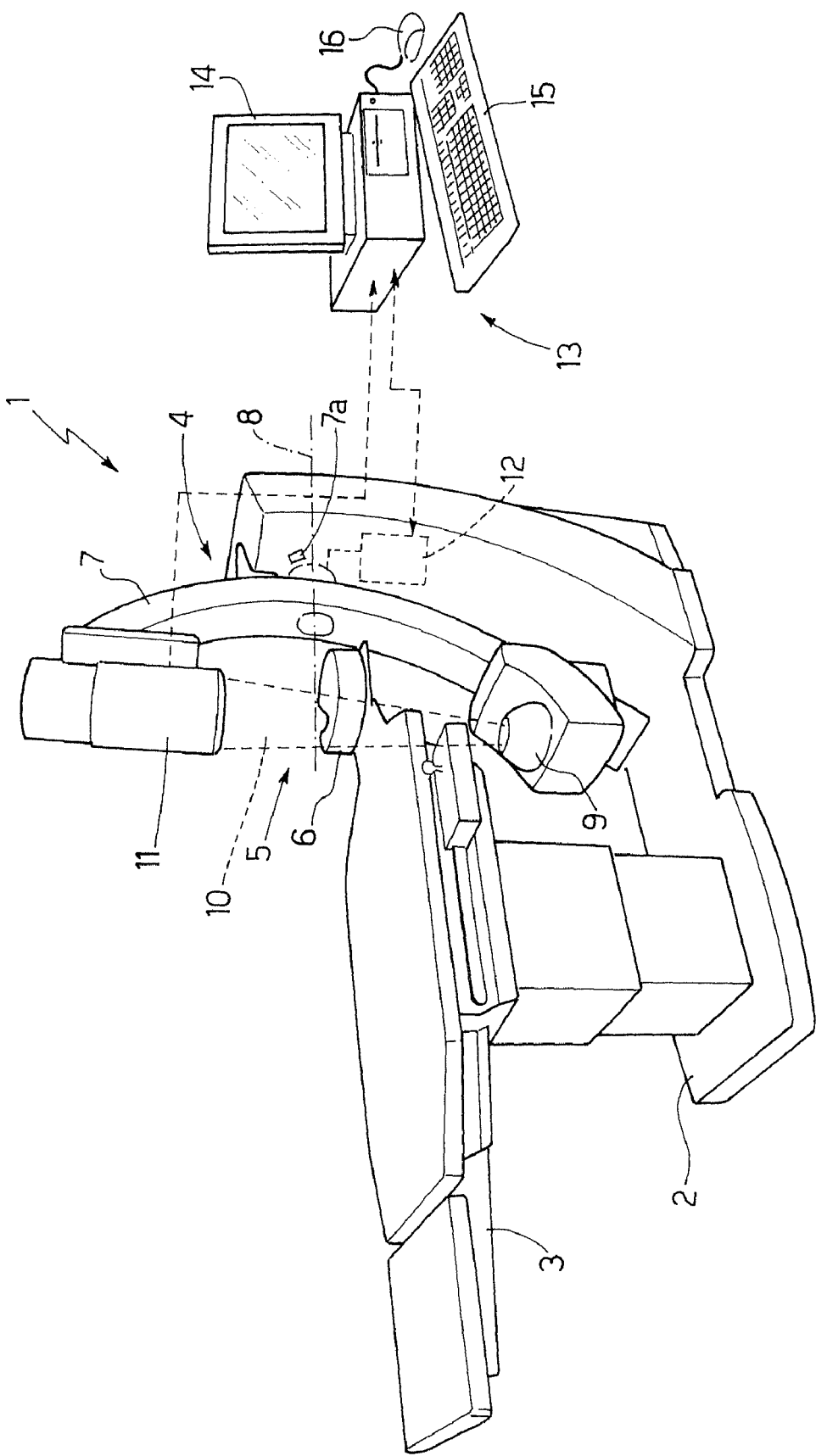
FIG. 1 illustrates a computed tomography scanner of the type used in dentistry.

In FIG. 1, designated as a whole by 1 is a computed tomography scanner of the type used in dentistry, comprising a frame 2, a couch 3 for supporting a patient (not illustrated) lying down, and an x-ray source-detector assembly 4, designed to rotate about an area of analysis 5 located in a region corresponding to a headrest 6 of the couch 3 for acquiring volumetric tomographic data of a part of the patient's head, for example a maxillofacial complex such as the dental arches, the mandibular bone, or else the maxillary bone of the patient, which hereinafter will be referred to as "object" for reasons of simplicity.

The source-detector assembly 4 comprises: a rotating support, constituted by an arm 7 mounted on the frame 2 and motor-driven so as to rotate about a substantially horizontal axis 8 of rotation traversing the region of analysis 5; a position sensor 7a for detecting the angular position of the arm 7 with respect to the axis 8; an x-ray emitter 9, mounted on a first end of the arm 7 and facing in the direction of the axis 8 for emitting a conical beam 10 of x-rays towards the area of analysis 5; and an x-ray detector 11, mounted on the opposite end of the arm 7 and facing in the direction of the axis 8 for receiving the beam 10 after it has traversed the area of analysis 5 and thus acquiring one or more radiographies of the object per unit angle of rotation.

The tomography scanner 1 further comprises a control unit 12, connected to the source-detector assembly 4 for controlling emission and reception of the beam 10 in a way synchronous with rotation of the arm 7, and a processing unit 13, connected to the detector 11 for receiving, storing, and processing the volumetric tomographic data so as to reconstruct images of the object and to the control unit 12 for activating the source-detector assembly 4 on the basis of commands imparted by an operator or of instructions with which the processing unit 13 itself is programmed. The processing unit 13 is constituted, for example, by a personal computer provided with a monitor 14 for displaying the reconstructed images, a keyboard 15, and a mouse 16 for acquiring data supplied and/or commands imparted by the operator.

Figure 2:
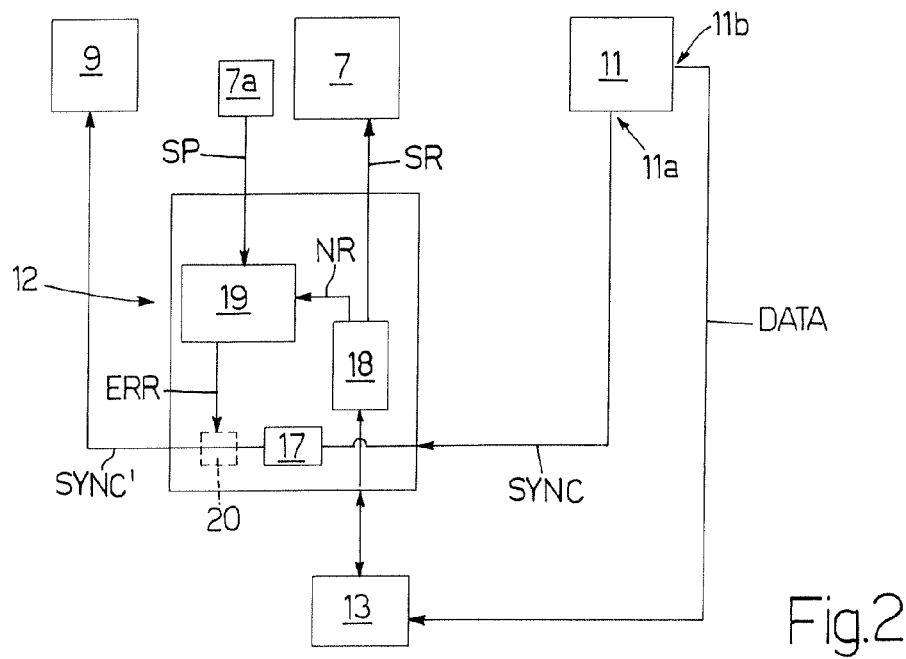
FIG. 2 illustrates a block diagram that describes the method for synchronising the emitter and the detector in the computed tomography scanner of FIG. 1 according to the present invention.

With reference to FIG. 2, the detector 11 has a first output 11a, designed to supply a synchronisation signal SYNC for controlling activation of the emitter 9 through a format conversion performed by the control unit 12. In other words, the emitter 9 is operated on the basis of the synchronisation signal SYNC. In particular, the control unit 12 implements a conversion block 17 for carrying out a conversion of the format of the synchronisation signal SYNC, said conversion being substantially transparent from the standpoint of the information content and producing a corresponding signal, designated by SYNC' in FIG. 2, which can be used directly by the emitter 9. From the functional standpoint, then, the emitter 9 is controlled directly by the detector 11 via the synchronisation signal SYNC.

The detector 11 moreover has a second output 11b, connected to the processing unit 13 for supply of the radiographies acquired, designated by DATA, to the processing unit 13 itself.

The synchronisation signal SYNC is constituted by a waveform that informs the emitter 9 of the periods of time in which the detector 11 is ready for acquiring radiographies. In other words, the detector (11) generates the synchronisation signal (SYNC), which corresponds to its state of activation for acquiring the radiographies, and the emitter (9) is controlled via the synchronisation signal (SYNC) in such a way that the beam of radiation (10) will be emitted when the detector (11) is already activated.

Figure 3:
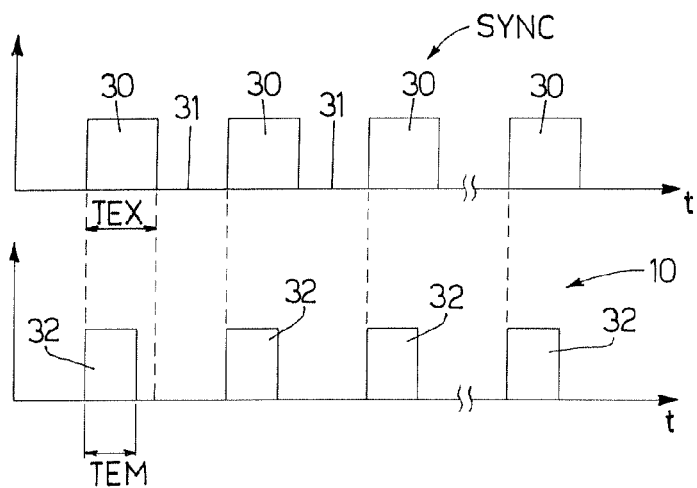
FIGS. 3 and 4 illustrate the waveforms of a synchronisation signal SYNC sent from the detector to the emitter, and a corresponding time plot of the x-ray beam emitted by the emitter according to the present invention.

With reference to FIG. 3, the synchronisation signal SYNC comprises a succession of activation pulses 30, during which the detector 11 is activated, i.e. it is ready for acquiring radiographies, in alternation with idle or de-activation periods 31, during which the detector 11 does not acquire any radiographies in so far as it transfers the radiographies acquired (DATA) to the processing unit 13. In other words, the detector 11 is operated for acquiring radiographies on the basis of synchronisation signal SYNC generated by the detector 11 itself. The activation pulses 30 each have a duration equal to a given exposure interval TEX characteristic of the detector 11. The duration of the exposure interval TEX is optionally configurable via the processing unit 13. The detector 11 is configured for continuous supply of the synchronisation signal SYNC as soon as it is electrically supplied.

The information content of the signal SYNC' is substantially the same as that of the synchronisation signal SYNC in the sense that the signal SYNC' comprises a succession of pulses (not illustrated) designed to activate the emitter 9, each pulse being synchronised with the rising edge of a corresponding activation pulse 30 generated by the detector 11.

The emitter 9 is configured for emitting the pulsed beam 10; in particular, the emitter 9 emits an x-ray pulse 32 as soon as it receives, via the signal SYNC', the rising edge of an activation pulse 30, i.e., after it has learned that the detector 11 is ready for acquiring a radiography. Consequently, the detector 11 functions as master, and the emitter 9 functions as slave. The x-ray pulse 32 has a duration of emission TEM that is established as a function of the dosage of x-rays required for acquiring the individual radiography. FIG. 3 illustrates the case where the duration of emission TEM is shorter than or equal to the exposure interval TEX so that the emitter 9 emits an x-ray pulse 32 at each activation pulse 30 comprised in a sub-succession of activation pulses 30 defined by the control unit 12 on the basis of instructions supplied by the processing unit 13.

Figure 4:
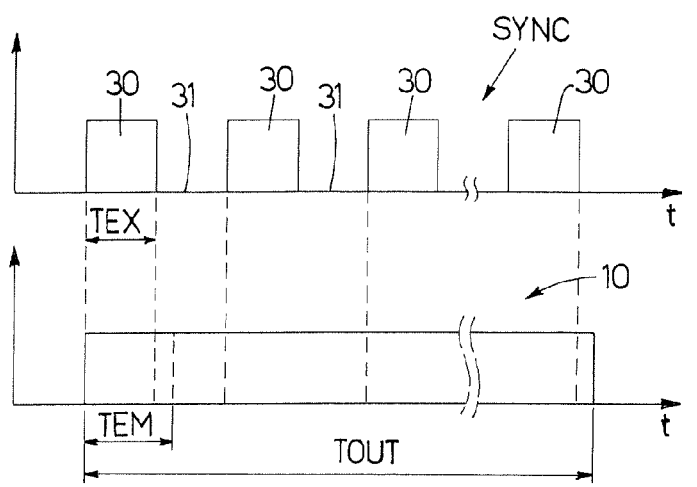

FIG. 4 illustrates, instead, the case where the duration of emission TEM is greater than the exposure time TEX. In these conditions, the emitter 9 is configured for emitting a beam 10 that is continuous in time, i.e., the emitter 9 remains turned on by a first usable activation pulse 30, defined by the control unit 12, until a time-out TOUT, defined as a function of the exposure interval TEX and of a total number of radiographies to be acquired established for analysis of the object. In this way, useless transients of turning-on and turning-off of the emitter 9 are prevented during the de-activation periods 31.

With reference once again to FIG. 2, the control unit 12 implements: a command block 18, designed to supply a command signal SR for issuing a command for rotation of the arm 7, and a number of radiographies NR per unit angle of rotation, said signal SR and number of radiographies NR being obtained by the command block 18 according to instructions received from the processing unit 13; and a verification block 19, which receives the synchronisation signal SYNC, the number of radiographies NR, and a position signal SP supplied by the position sensor 7a, and supplies at output an error signal ERR, which informs whether the current number of radiographies acquired is correct. In particular, the verification block 19 is configured for counting the number of radiographies acquired, starting from the synchronisation signal SYNC and compares said number with a value obtained as a function of the number of radiographies NR and of the position signal SP.

The control unit 12 moreover implements an inhibition block 20, designed to inhibit, on the basis of the error signal ERR, propagation of the synchronisation signal SYNC to the emitter 9 in the case where the current number of radiographies acquired is not correct. In this way, emission of useless doses of x-rays is blocked when the source-detector assembly 4 does not function correctly.

Operation of the source-detector assembly 4 of the tomography scanner 1 described above does not require further explanations in so far as it results clearly from the foregoing description.

From the above description, it is moreover clear that the method for synchronisation between the emitter 9 and the detector 11 of a tomography scanner 1 according to the present invention is applicable to any type of tomography scanner and not only to a tomography scanner for use in dentistry, and for acquiring radiographies of any part of the human body or of any object of biological or non-biological matter. In fact, the method is completely independent of the type of mechanical structure of the tomography scanner 1 and of the technology of emission and detection of radiation used in the emitter 9 and in the detector 11, respectively.

The main advantage of the method for synchronisation between emitter and receiver of a tomography scanner described above is that of not requiring generation of a synchronisation signal by an external unit, said generation being a source of frequent synchronisation errors that lead to errors of acquisition and hence administration of useless doses of x-rays to the patient. In addition, the detector 11 according to the present invention can be simply integrated in any tomography scanner 1 with minimum modifications of the electronics of the control unit 12.

The invention claimed is:

1. A method for synchronizing an emitter and a detector in a computed tomography scanner, wherein the emitter is configured to emit a beam of a given radiation through an object to be analysed, and the detector is configured to receive said beam after the beam has traversed the object, such that radiographies of the object are acquired, said method comprising:
   generating a synchronisation signal;
   operating the detector and the emitter for acquiring radiographies on the basis of said synchronisation signal;
   wherein said synchronization signal is generated autonomously by the detector such that the detector operates as a master and the emitter operates as a slave in acquiring the radiographies.

2. The method according to claim 1, wherein said synchronization signal comprises a succession of activation pulses, during which said detector is ready for acquiring radiographies, in alternation with de-activation periods, during which the detector does not acquire any radiography.

3. The method according to claim 2, wherein each of said activation pulses has a duration equal to a given exposure interval characteristic of said detector.

4. The method according to claim 3, further including the step of said emitter emitting a radiation pulse presenting a duration of emission shorter than or equal to said exposure interval;
- wherein said beam of radiation is emitted in the form of pulses, each of which is emitted in response to the rising edge of a corresponding activation pulse.

5. The method according to claim 3, further including the step of said emitter emitting a radiation pulse presenting a duration of emission longer than said exposure interval;
- wherein said beam of radiation being emitted in a continuous way starting from the rising edge of a first activation pulse until a time-out, defined as a function of the exposure interval and of a total number of radiographies to be acquired.

6. The method according to claim 1, further including the step of said detector supplying said synchronization signal as soon as the detector itself is electrically supplied.

7. The method according to claim 1, wherein the operating further includes converting the synchronization signal to a format suitable to be used by the emitter.

8. The method according to claim 1, wherein said computed tomography scanner comprises supporting means rotating about an axis configured to support said emitter and detector and to rotate the emitter and the detector about said object to be analyzed said method further including the steps of:
- detecting an angular position of said supporting means;
- verifying the correctness of a current number of radiographies acquired as a function of the angular position, of said synchronisation signal, and of a number of acquisitions per pre-defined unit angle; and
- inhibiting propagation of said synchronisation signal to said emitter for blocking emission of said beam if the current number of radiographies acquired is not correct.

9. A detector for a computed tomography scanner, wherein the computed tomography scanner includes an emitter configured to emit a beam of a given radiation through an object to be analyzed;
- wherein the detector is configured to receive said beam after the beam has traversed the object; and
- the detector is further configured so as to autonomously generate a synchronization signal for controlling operation of the emitter and the detector such that the detector operates as a master and the emitter operates as a slave for the purpose of acquiring radiographies of said object.

10. The detector according to claim 9, comprising an output configured to supply said synchronisation signal as soon as the detector is electrically supplied.

11. A computed tomography scanner comprising an emitter designed to emit a beam of a given radiation through an object to be analysed, and a detector designed to receive said beam after the beam has traversed the object so as to acquire radiographies of the object; wherein the detector is of the type claimed in claim 9.

12. The computed tomography scanner according to claim 11, comprising:
- a rotating supporting means rotating about an axis so as to support said emitter and detector and configured to rotate the emitter and the detector about said object to be analyzed;
- a position sensor means configured to supply a position signal corresponding to an angular position of said supporting means; and
- a control means configured to receive the position signal and said synchronisation signal to propagate the synchronisation signal to the emitter, and further configured to verify a correctness of a current number of acquired radiographies as a function of the angular position, said synchronization signal, and a number of acquisitions per a pre-defined unit angle, and to inhibit propagation of said synchronisation signal to said emitter such that emission of said beam is blocked if the current number of radiographies acquired is not correct.

13. The computed tomography scanner according to claim 12, wherein said control means comprise conversion means configured to receive said synchronisation signal and to convert the synchronisation signal to a format suitable to be used by the emitter.

14. A computed tomography scanner for use in dentistry according to claim 11.

15. A method for synchronizing an emitter and a detector in a computed tomography scanner wherein the emitter is configured to emit a beam of a given radiation through an object to be analyzed, and the detector is configured to receive said beam after the beam has traversed the object, to acquire radiographies of the object, said method comprising:
- the detector generating a synchronization signal, wherein the synchronization signal comprises a succession of activation pulses, during which said detector is ready for acquiring radiographies, in alternation with de-activation periods, during which the detector does not acquire any radiography;
- operating the detector and the emitter on the basis of said synchronization signal;
- wherein each of said activation pulses has a duration equal to a given exposure interval characteristic of said detector; and
- said emitter emitting a radiation pulse presenting a duration of emission longer than said exposure interval.

* * * * *